United States Patent [19]

Piraka

[11] Patent Number: 5,632,751
[45] Date of Patent: May 27, 1997

[54] SURGICAL SUTURING DEVICE

[76] Inventor: Hadi A. Piraka, 21257 Woodfarm, Northville, Mich. 48167

[21] Appl. No.: 508,669

[22] Filed: Jul. 28, 1995

[51] Int. Cl.$^6$ .................................................. A61B 17/10
[52] U.S. Cl. ...................... 606/139; 606/142; 606/143
[58] Field of Search .................................. 606/139, 144, 606/147, 140, 142, 145, 146, 143

[56] References Cited

U.S. PATENT DOCUMENTS

| | | |
|---|---|---|
| 1,037,864 | 9/1912 | Carlson et al. . |
| 1,131,163 | 3/1915 | Saunders et al. . |
| 3,090,386 | 5/1963 | Curtis ...................................... 606/144 |
| 4,236,470 | 12/1980 | Stenson . |
| 5,454,823 | 10/1995 | Richardson et al. ..................... 606/148 |
| 5,480,406 | 1/1996 | Nolam et al. ............................ 606/139 |

*Primary Examiner*—Michael Buiz
*Assistant Examiner*—Kevin Truong
*Attorney, Agent, or Firm*—Alex Rhodes

[57] ABSTRACT

A surgical suturing device for closing a wound or an incision having a first elongated needle holder having an end portion for grasping and releasing a thread end of a needle and a second elongated needle holder pivotally connected to the first elongated needle holder having an end portion for grasping and releasing an opposite pointed end portion of the needle. One end portion of an elongated rod is connected to pair of needle holders and moves the needle holders together and away from each other. An opposite end portion of the rod is attached to a pivotally attached handle which moves the rod. In each of the needle holders there is a latch which is actuated when the needle holders are brought together to simultaneously grasp one end portion of the needle and release the opposite end portion of the needle.

9 Claims, 7 Drawing Sheets

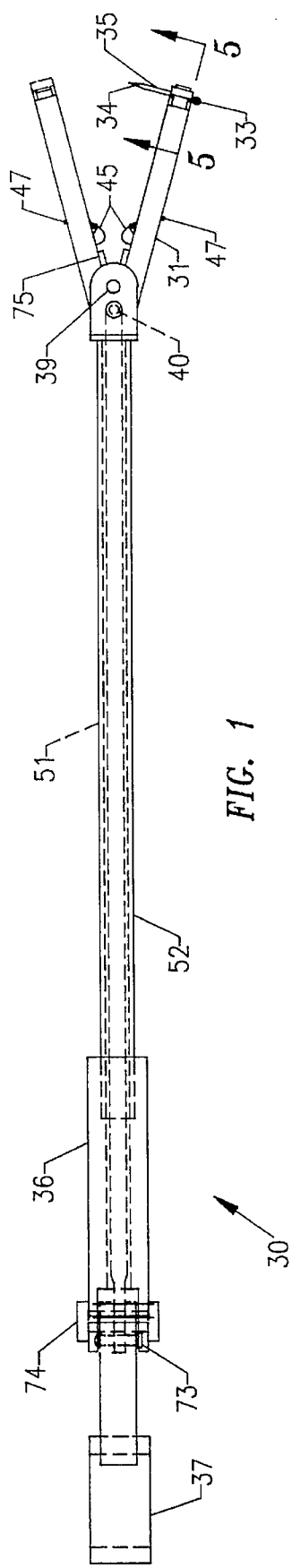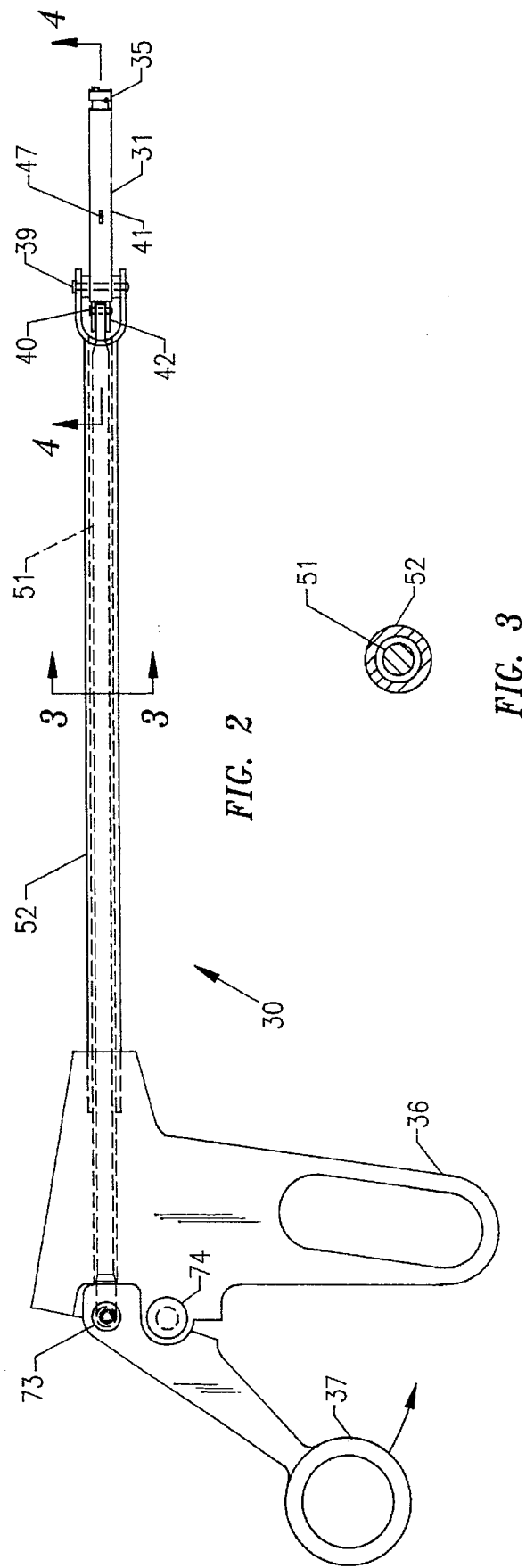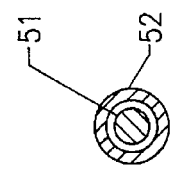
FIG. 1
FIG. 2
FIG. 3

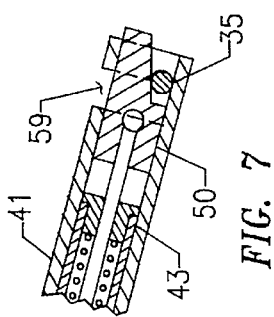
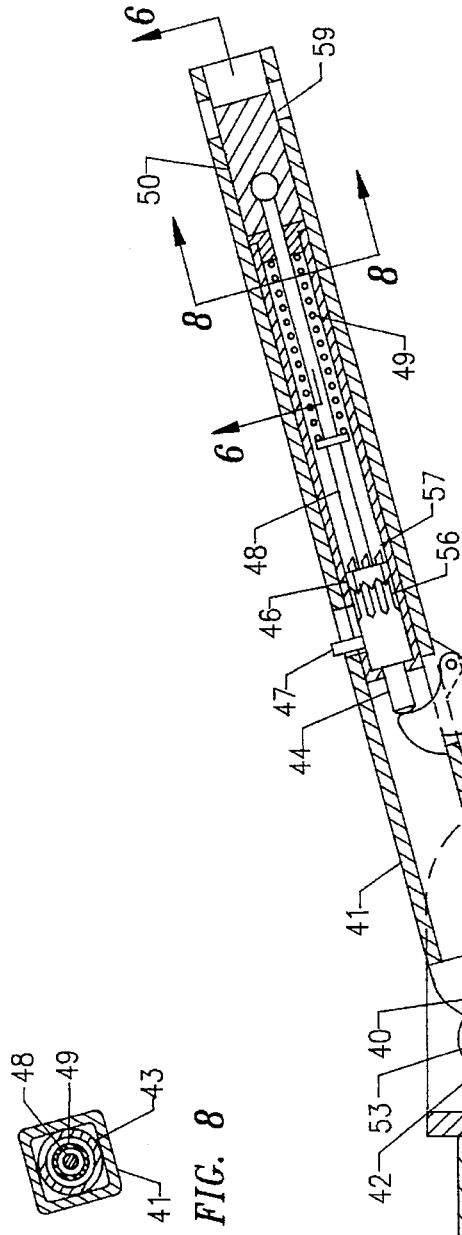
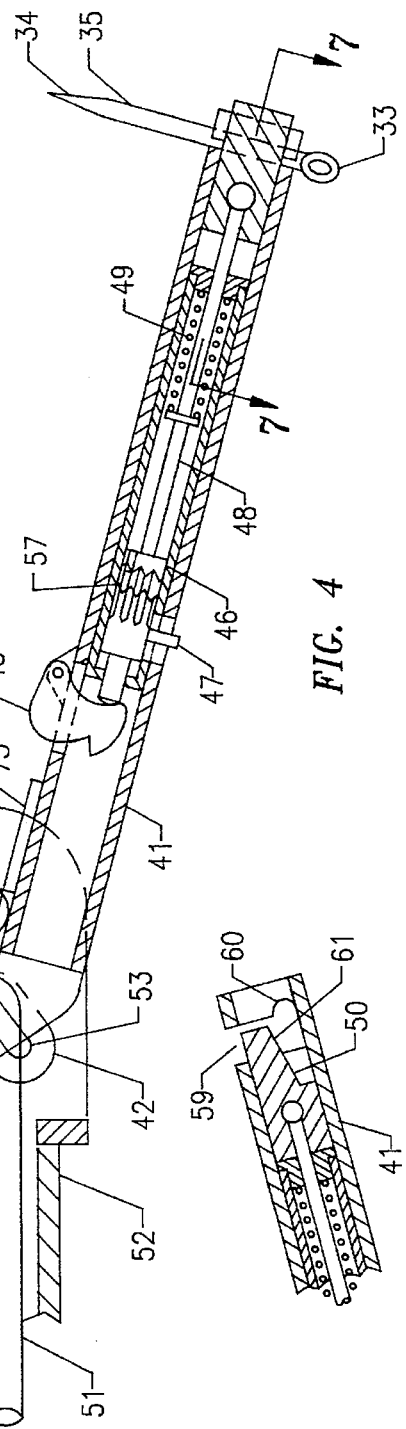
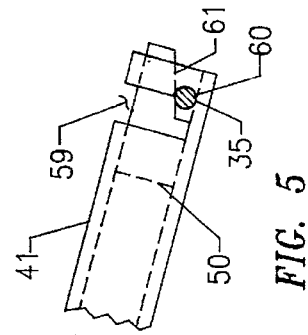
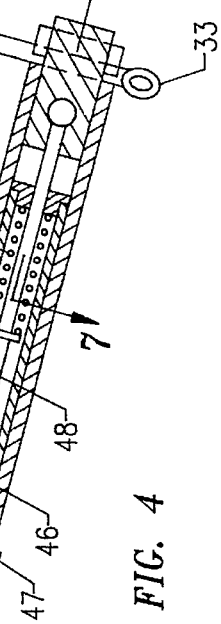
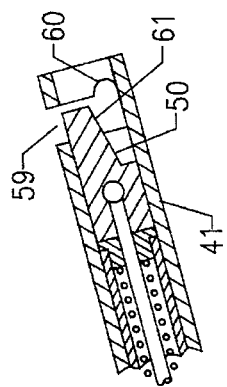

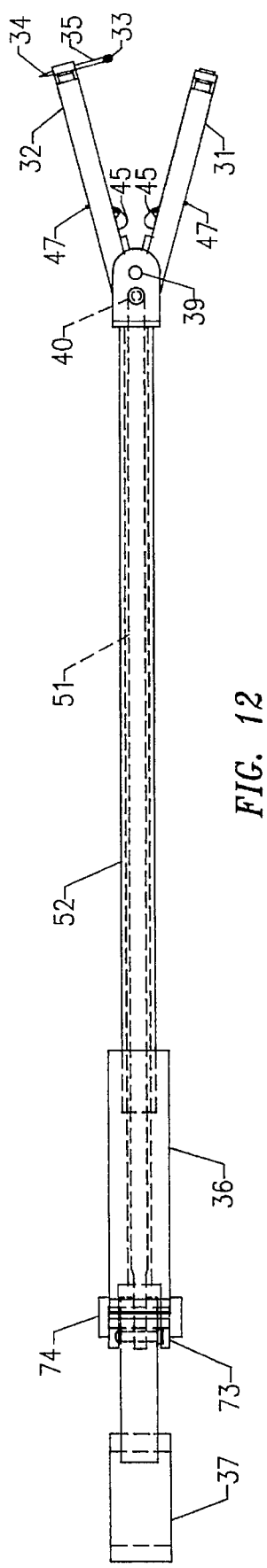
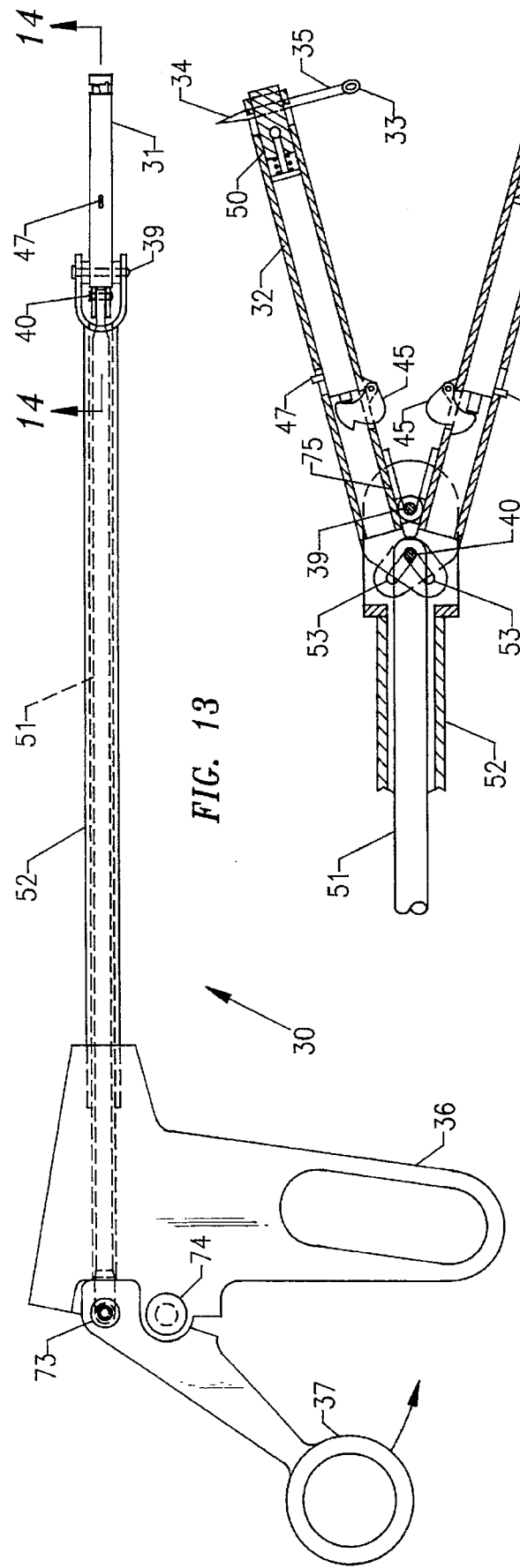
FIG. 12
FIG. 13
FIG. 14

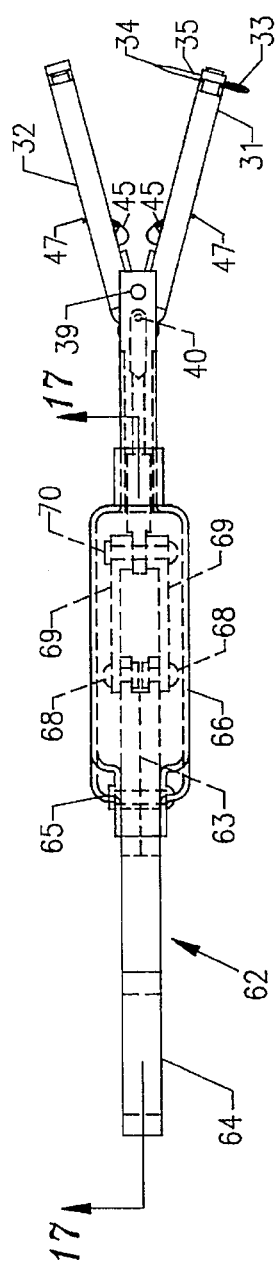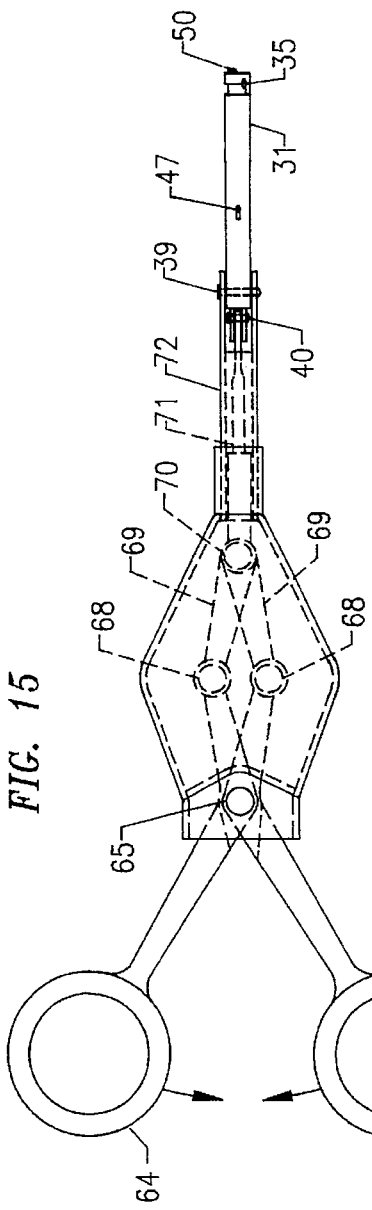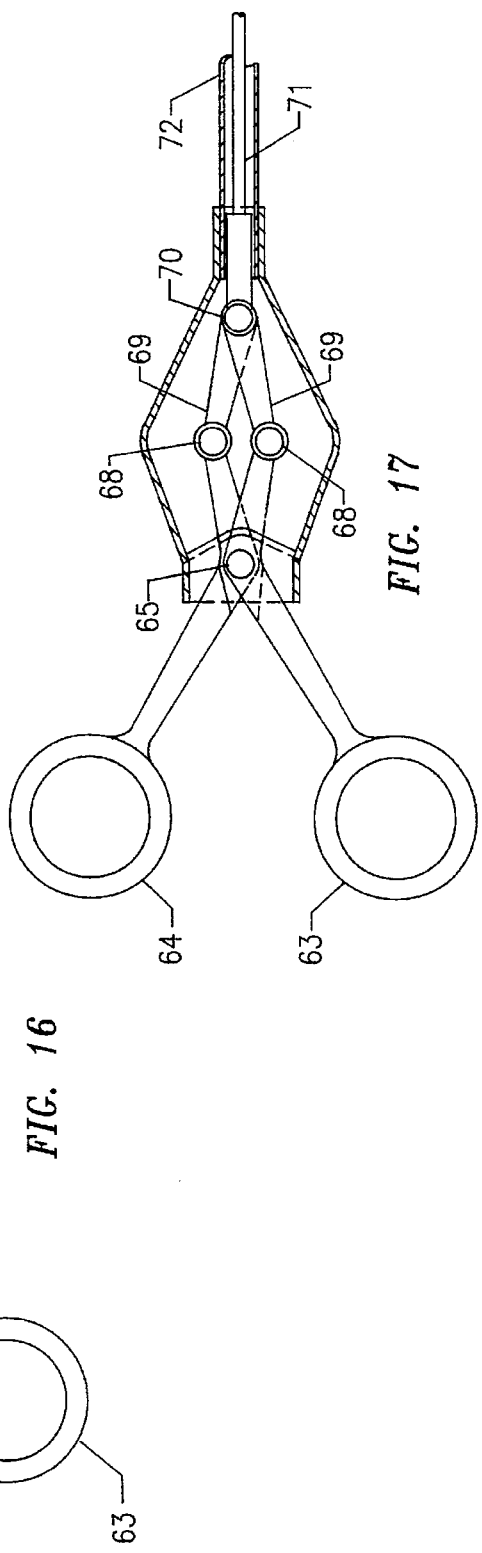

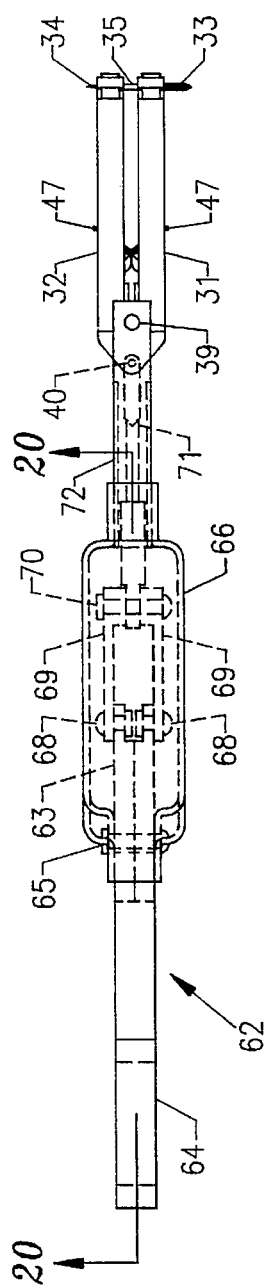
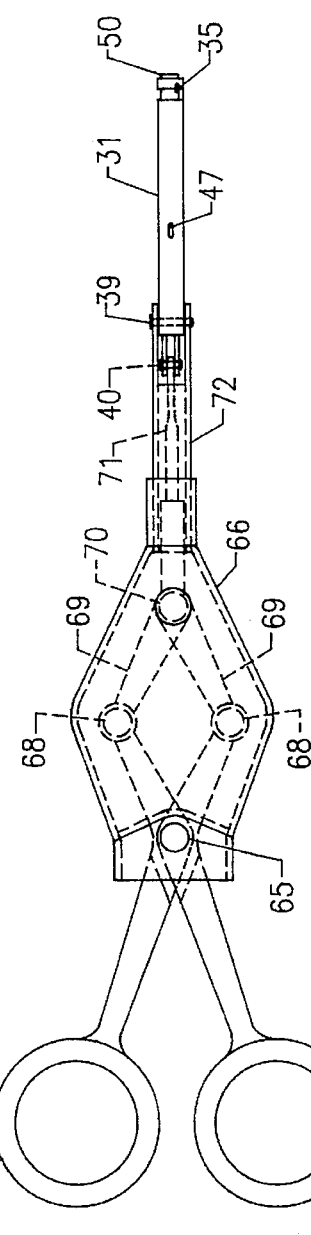
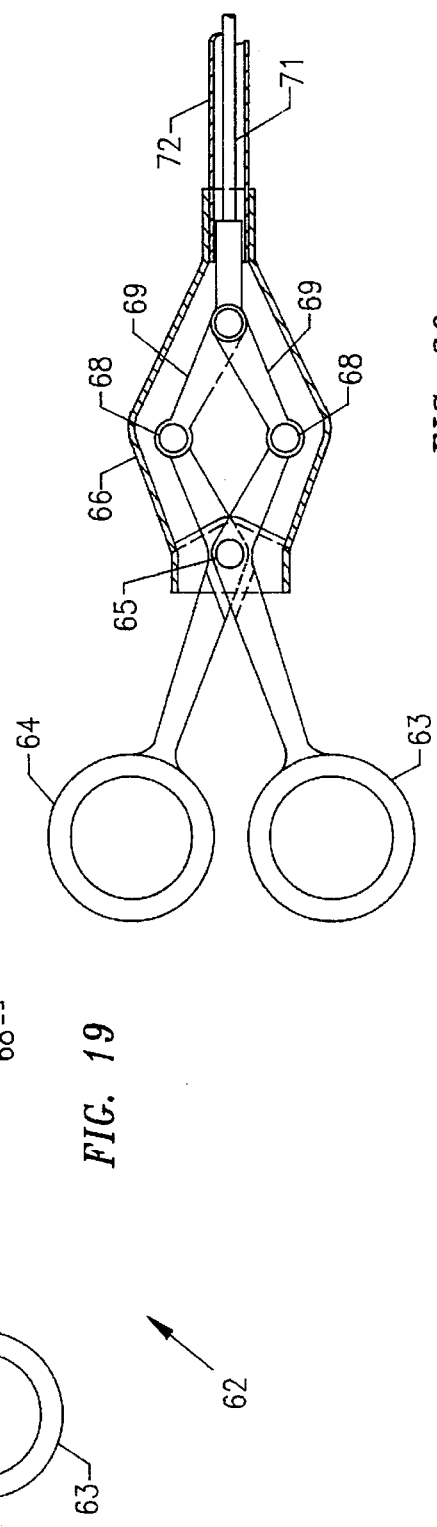
FIG. 18
FIG. 19
FIG. 20

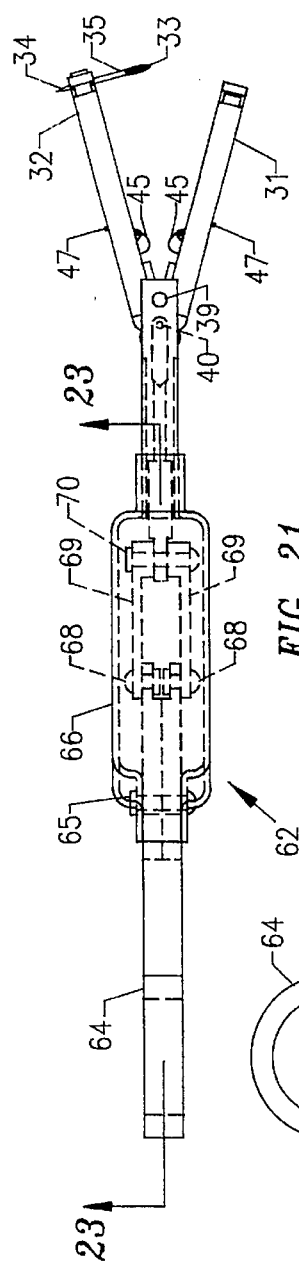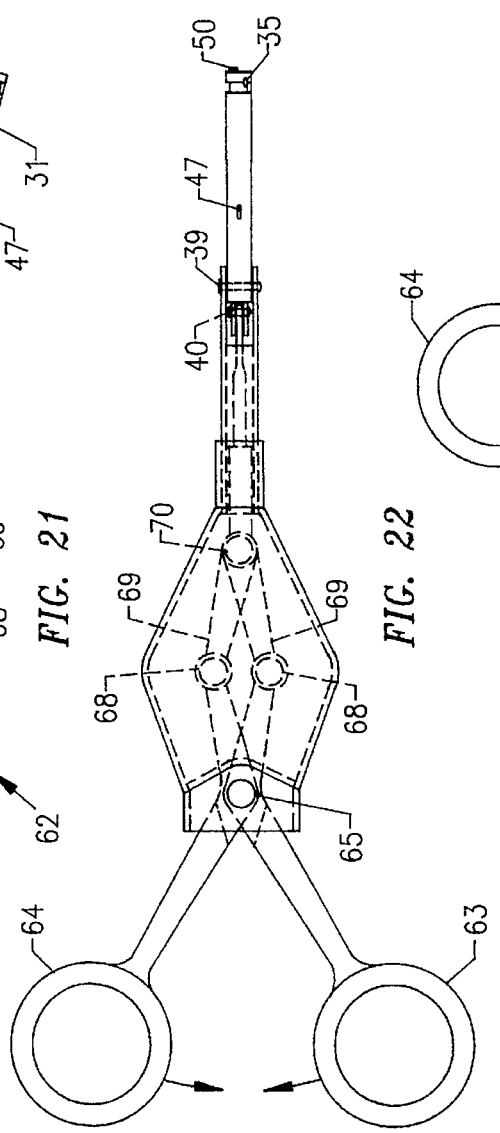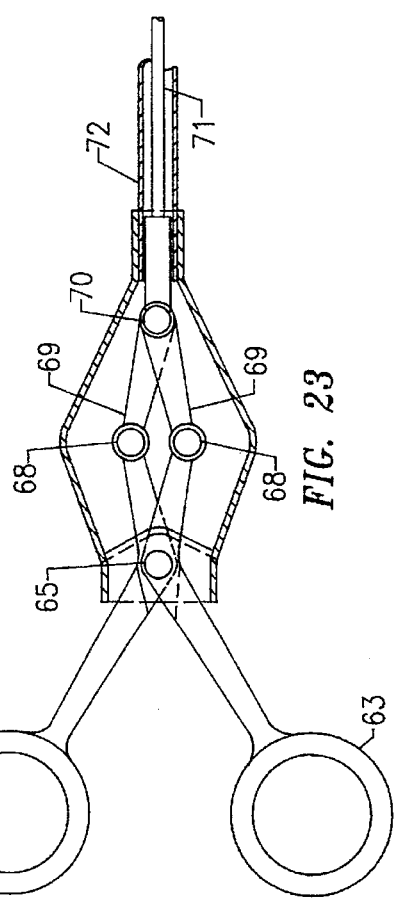
FIG. 21
FIG. 22
FIG. 23

SURGICAL SUTURING DEVICE

FIELD OF THE INVENTION

This invention relates to surgical needle holders and more particularly to a surgical device for suturing wounds and incisions.

BACKGROUND OF THE INVENTION

Needle holders are suturing devices which surgeons use for closing wounds and incisions. One limitation of current needles is that auxiliary devices, such as forceps, are used for grasping and pulling needles through tissues. In some cases, assistants are used for grasping the pointed ends of needles and pulling them through tissues.

A surgeon must view the surgery through a telescope or on a TV camera during endoscopic surgery and only a limited space is available for maneuvering needle holders and forceps. Skill and dexterity are required to close incisions with current needle holders and prevent injuries to patients. The limited space, limited maneuverability and restricted viewing make the tying of knots difficult and time consuming.

Another problem with current needle holders is that the use of two hands for suturing restricts surgeons from using one hand for holding different structures.

SUMMARY OF THE INVENTION

The present invention overcomes the foregoing problems by providing a suturing device which takes over the function of a surgeon's hand of grasping forceps. Although the improved suturing device is particularly useful for endoscopic surgery, it provides substantial benefits during general surgery.

One feature of the invention is that only one hand is used during endoscopic surgery for tying knots and closing incisions. This frees one hand for performing other tasks, such as holding other structures.

One benefit is that the tying of knots is made easier by looping a needle into a suture.

Another benefit is that the time for performing surgical procedures is reduced, thereby reducing stresses on patients and allowing for greater utilization of operating rooms.

The invention resides in several novel features which individually and collectively contribute to its ability to perform suturing of incisions and wounds. One characteristic feature of the invention is that a pair of needle holders simultaneously grasp and release opposite ends of a needle during the closing of a wound or incision. Another characteristic feature is that only one hand is required for closing a wound or incision.

In the first aspect of the invention which is particularly useful for endoscopic surgery, the invention broadly comprises a pair of pivotally connected needle holders for simultaneously grasping and releasing opposite ends of a surgical needle, a fixed and a movable handle for axially moving a slender rod to rotate the needle holders, and a long slender rod connected at one end thereof to the movable handle and at the other end thereof to the needle holders.

In the second aspect of the invention which is useful for general surgery, a pair of movable handles are connected by a pair of links to a slender rod. The rod is connected to a pair of needle holders which simultaneously grasp and release end portions of a surgical needle.

Further benefits and features of the invention will become apparent from the ensuing detailed description and drawings which disclose the invention. The property in which exclusive rights are claimed is set forth in each of the numbered claims at the conclusion of the detailed description.

BRIEF DESCRIPTION OF THE DRAWINGS

The invention will be better understood and further objects, characterizing features, details and advantages thereof will appear more clearly with reference to the diagrammatic drawings illustrating a presently preferred specific embodiment of the invention by way of non-limiting example only.

FIG. 1 is a top view of an endoscopic suturing device and surgical needle in accordance with the present invention.

FIG. 2 is a front elevational view of the device shown in FIG. 1.

FIG. 3 is an enlarged cross-sectional view taken on the line 3—3 in FIG. 2.

FIG. 4 is an enlarged cross-sectional view taken on the line 4—4 in FIG. 2.

FIG. 5 is an enlarged cross-sectional view taken on the line 5—5 in FIG. 1.

FIG. 6 is an enlarged cross-sectional view taken on the line 5—6 in FIG. 4.

FIG. 7 is an enlarged cross-sectional view taken on the line 7—7 in FIG. 4.

FIG. 8 is an enlarged cross-sectional view taken on the line 8—8 in FIG. 4.

FIG. 12 is a top view of the suturing device of FIG. 1 shown in a third operative condition.

FIG. 13 is a front elevational view of the suturing device in the third operative condition.

FIG. 14 is an enlarged cross-sectional view taken on the line 14—14 in FIG. 13.

FIG. 15 is a top view of an alternate embodiment and needle for performing general surgery in which a wound or incision is readily accessible.

FIG. 16 is a front elevational view of the device shown in FIG. 15.

FIG. 17 is a cross-sectional view taken on the line 17—17 in FIG. 15.

FIG. 18 is a top view of the alternate embodiment of FIG. 15 shown in a second operative condition.

FIG. 19 is a front elevational view of the alternate embodiment in the second operative condition.

FIG. 20 is a cross-sectional view taken on the line 20—20 in FIG. 18.

FIG. 21 is a top view of the alternate embodiment of FIG. 15 shown in a third operative condition.

FIG. 22 is a front elevational view of the alternate embodiment in the third operative condition.

FIG. 23 is a cross-sectional view taken on the line 23—23 in FIG. 21.

DETAILED DESCRIPTION OF THE PREFERRED EMBODIMENT

Figure 9:
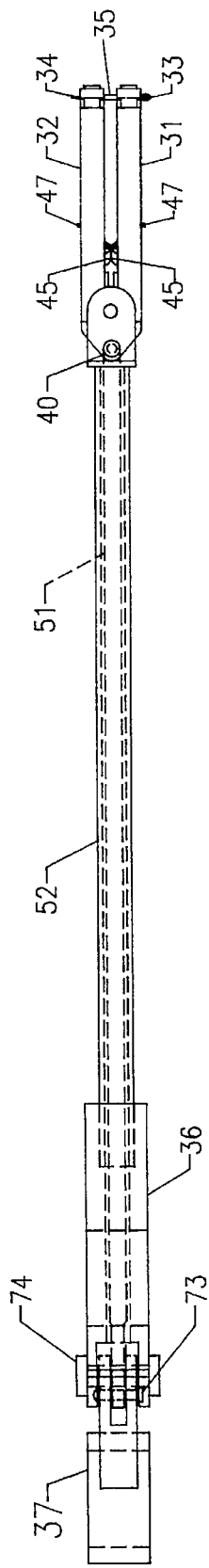
FIG. 9 is a top view of the suturing device of FIG. 1, shown in a second operative condition.

Referring now to the drawings wherein like numerals designate like and corresponding parts throughout the several views, an endoscopic surgical suturing device 30 and needle 35 are shown in FIGS. 1 through 14, inclusive, according to my invention. The needle 35 may be any of the various types used in surgery. By way of example, the needle 35 may be straight or slightly curved. The needle 35 may also have an eye end portion or may be part of a needle and thread assembly wherein a thread is permanently joined to the thread end portion 33 of the needle 35.

One characteristic feature of my suturing device 30 is that a pair of needle holders 31, 32 simultaneously grasp and release the "thread" end portion 33 and "pointed" end portion 34 of the needle 35. With reference to FIGS. 1–15, inclusive, the needle holders 31, 32 are pivotally connected with a pin 39.

Attached to end portions of the needle holders 31, 32 by a second pin 40 is a slender rod 51 which is mounted in a cylindrical thin wall tube 52. An opposite end portion of the rod 51 is connected with a pin 73 to a movable handle 37 which is pivotally connected with a pin 74 to a fixed handle 36. When the movable handle 36 is pivoted toward and away from the fixed handle 36, the rod 51 moves back and forth in the tube 52. An upper end portion of the tube 52 is rigidly attached to the fixed handle 36.

Figure 10:
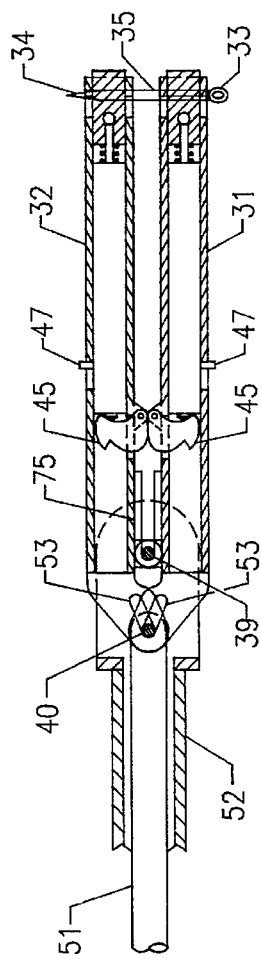
FIG. 10 is a front elevational view of the suturing device in the second operative condition.
Figure 11:
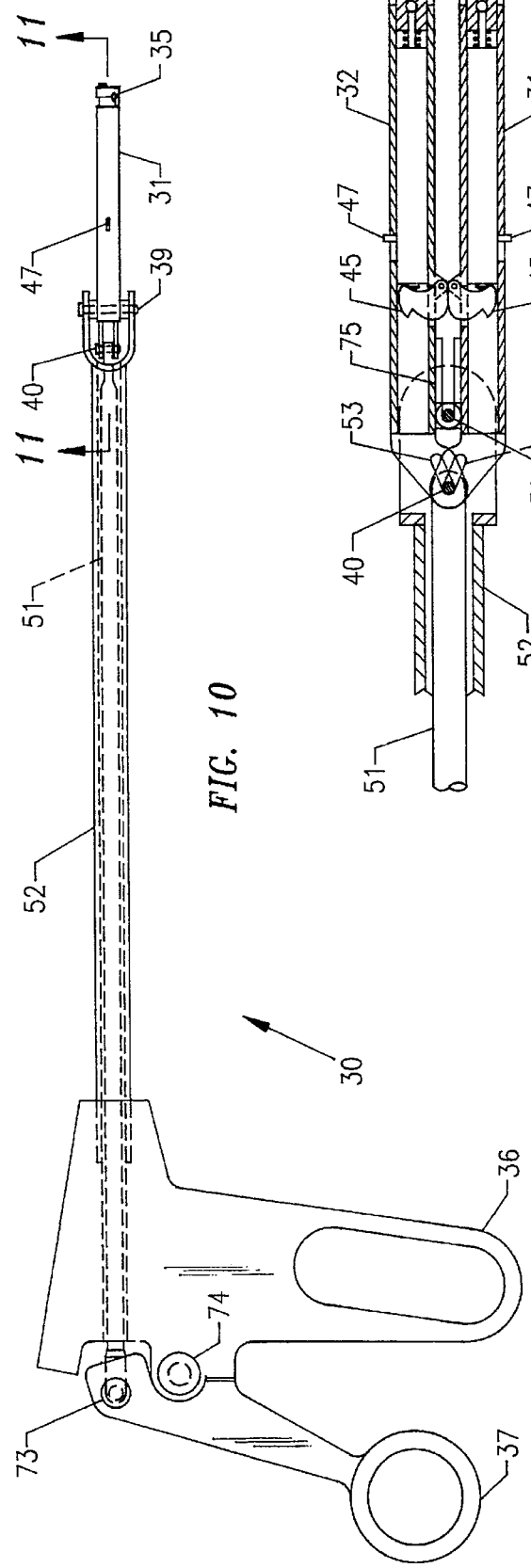
FIG. 11 is an enlarged cross-sectional view taken on the line 11—11 in FIG. 10.

Referring to FIGS. 9–11, when the needle holders 31, 32 are adjacent to each other, the slender rod 51, tube 52, and needle holders 31, 32 are preferably about 30 cm long, and about 9 to 11 mm wide, in order to pass through a standard 10 to 12 mm cannula.

The positions of the needle holders 31, 32 during the making of a stitch are shown in FIGS. 1, 9 and 12. With reference to FIG. 1, at the initial condition, a thread end portion 33 of a needle 35 is held in one of the needle holders 31 and the needle holders 31, 32 are separated from each other. As shown in FIG. 2, the movable handle 37 is farthest away from the fixed handle 36.

In the second condition, as shown in FIG. 9, the needle holders 31, 32 are adjacent to each other, and the movable handle 37 is closest to the fixed handle 36. In the third condition, as shown in FIG. 12, a pointed end portion 34 of the needle is held in the other needle holder 32, the needle holders 31, 32 are separated from each other, and the movable handle is farthest away from the fixed handle 36.

The needle holders 31, 32 are similar and their construction is best understood by reference to FIGS. 4 through 8. Each needle holder 31, 32 is comprised of a rectangular outer tube 41, a slotted bracket 42 attached to an end portion of the rectangular tube 41, a cylindrical inner tube 43, a plunger 44, a cam 45, a latch 46, a short manual latching pin 47, a cylindrical latching rod 48, a helical spring 49, and a wedge 50.

The pin 39 which connects the two needle holders 31, 32 is attached to inner walls of the rectangular tubes 41. The pin 40 extends through the angular slots 53 of the brackets 42 and an end portion of the rod 51.

When the movable handle 37 is moved toward the fixed handle 36, the rod 51 moves axially rearward, causing the pin 40 to move rearward in the angular slots 53 and the needle holders 31, 32 to rotate inwardly toward each other to the position shown in FIG. 9. During the inward rotation of the needle holders 31, 32, the cams 45 contact and rotate, causing the plungers 44 to move axially forward in the tube 43 and causing one of the needle holders 31 to latch and the other of the needle holders 32 to unlatch. When pressure on the movable handle 37 is released, the flat leaf spring 75 causes the needle holders 31, 32 to separate from each other. During the separation of the needle holders 31, 32, the cams 45 are free to move outwardly, allowing the plunger 44 of unlatched needle holder 32 to move rearwardly.

The latching and unlatching of the needle holders 31, 32 is similar to a mechanism of many ball point pens. Referring to FIG. 4, on the sides of the plunger 44 and latch 46 are external splines 56. The external splines 56 on the plunger 44 and latch 46 engage internal splines 57 of the tube 43. Alternate spline teeth on the latch 46 are omitted, resulting in their being twice the number of spline teeth on the plunger 44 as the latch 46. Alternate spaces of the internal splines 57 of the tube 43 are blocked off, such that the latch 46 is prevented from moving rearward on the internal splines 57 when the latch 46 rotates after passing through the internal splines 57.

At the bottom of the plunger 44 are radial serrations 54 which engage radial serrations 55 of the latch 46. When the plunger 44 and latch 46 are urged forwardly by the cam 45, helical spring 49 is compressed. After the latch 46 has cleared the internal splines 57 of the tube 43, the latch 46 is caused to rotate a small amount by the serrations 54 of the plunger 44. When the latch 46 is allowed to retract a small amount by a small movement of the handle 37, the spline teeth 56 of the latch 46 engage the blocked spaces of tube 43, thereby preventing the latch 46, spring 49, rod 48 and wedge 50 from releasing and returning to their rearmost positions.

When the plunger 44 is moved forward by the cam 45 a second time, the latch 46 again rotates to allow the rod 48, plunger 44, spring 49 and wedge 50 to return to their rearmost positions. The plungers 44 can also be latched and unlatched by moving the manual latching pins 47 which extend outwardly from the outer sides of the needle holders 31, 32.

With reference to FIG. 4, the forward end of the rod 48 of each needle holder is attached to the wedge 50. As shown in FIGS. 4 and 6, in the end of the needle holder outer tubes 41 are transverse slots 59 which allow the needle 35 to enter the needle holders 31, 32. The slots also allow the surgeon to observe whether the end of a needle 35 is engaged with the needle holders 31, 32.

The forward end portions of the outer tubes 41 form bridge-like supports for the ends of the wedges 50 when the wedges 50 are in the latched positions. At the bottoms of the slots 59 are small arcuate notches 60 which improve the retention of ends 33, 34 of needles 35. When the wedges 50 are in the forward latched positions, tapered lower surfaces 61 of the wedges 50 press against the end portions 33, 34 of the needles 35. The wedges 50 are preferably made of a semi-rigid polymer whereby the wedges can slightly compress and grasp the ends of the needles.

During endoscopic surgery, the suturing device 30 is used in the following manner. With reference to FIGS. 1–3, the needle holders 31, 32 are brought together by gripping the suturing device 30 with one hand and moving the fixed 36 and movable 37 handles together. The thread end 33 of a needle 35 is mounted in one of the needle holders 31 by moving the latch pin 47 forward to latch the wedge 50 against the thread end 33 of the needle 35. The wedge 50 of the other needle holder 32 is released by moving its latch pin 47 forward.

With the needle holders 31, 32 held adjacent to each other, the needle 35, needle holders 31, 32 and tube 52 are inserted through a 10–12 mm cannula. The needle holders 31, 32 are next opened by releasing the pressure on the movable handle 37, thereby allowing the leaf spring 75 to separate the needle holders 31, 32. The needle holders 31, 32 are positioned across an incised structure (e.g. fallopian tube, ovary, uterine wall, etc.) and the pointed end 34 of the needle 35 is passed through one edge of the incised structure by laterally moving the suturing device 30.

The needle holders 31, 32 are gradually brought together to pass the pointed end 34 of the needle 35 through the opposite side of the incision and engage the cams to simultaneously release the thread end 33 and grasp the pointed end 34 of the needle 35. This sequence is repeated to produce additional stitches and close the incision. The suturing device 30 may also be used by bringing the needle holders 31, 32 together with their end portions unlatched, inserting the needle holders 31, 32 through a cannula, inserting a needle through another opening into the patient, attaching the threaded end portion 33 of the needle 35 to one of the needle holders 31 and latching the needle holder 31.

With reference to FIGS. 15 through 23, an alternate embodiment 62 is shown which is adapted for general surgeries in which wounds or incisions are easily accessible. In this embodiment 62, a pair of symmetrical handles 63, 64 are pivotally connected by a pin 65 in a housing 66. The forward end portions 67 of the handles 63, 64 are pivotally connected by pins 68 to a pair of intermediate links 69. The forward ends of the intermediate links 69 are attached with a pin 70 to a short rod 71 inside of a short rectangular tube 72 which is attached to the housing 66. The forward end of the short rod 71 is connected by a pin 40 which is joined to the pivotally connected needle holders 31, 32, previously described.

In FIGS. 15 through 17, the suturing device 62 is shown with the needle holders 31, 32 separated and the thread end portion 33 of the needle 35 held in one of the needle holders 31. In FIGS. 18 through 20, the suturing device 62 is shown with the needle holders 31, 32 adjacent to each other for forcing the pointed end through the tissue and gripping the pointed end 34 of the needle, and in FIGS. 21 through 23, the suturing device 62 is shown with the needle holders 31, 32 separated for pulling the needle 35 through the tissue.

From the foregoing it will be apparent that my invention provides a suturing device having substantial benefits for endoscopic and general surgery. Although only two embodiments have been illustrated and described, it is not my intention to limit the scope of my invention to these embodiments, since other embodiments can be developed by changes in material and shape as well as substitution and arrangements of parts without departing from the spirit thereof.

I claim:

1. A surgical suturing device comprising: a needle having a thread end portion and an opposite pointed end portion; a pair of needle holders including a first elongated needle holder, said first needle holder having an end portion for grasping and releasing said thread end portion of said needle and a second elongated needle holder pivotally connected to said first needle holder and having an end portion for grasping and releasing said opposite pointed end portion of said needle, said needle holders being selectively movable between a closed position wherein said needle holders are adjacent to each other and an open position wherein said needle holders are angularly displaced apart from each other; a means actuated by moving said needle holders to said closed position for simultaneously grasping said thread end portion of said needle in said first needle holder and releasing said pointed end portion in said second needle holder and thereafter simultaneously grasping said pointed end portion and releasing said thread end portion; and a pair of handles for selectively moving said needle holders between said closed and said open positions.

2. The surgical suturing device recited in claim 1 wherein said means for grasping and releasing said needle's end portion comprises in each of said needle holders a wedge for engaging an end portion of said needle and a latch for engaging and releasing said wedge.

3. The surgical suturing device recited in claim 2 further comprising in each of said needle holders a cam for operating said latch.

4. The suturing device recited in claim 1 further comprising a pair of links, each of said links having an end portion connected to an end portion of one of said handles and an opposite end portion connected to an opposite end portion of said other handle for moving a rod in an axial direction; a rod having one end portion connected to said interconnected end portions of said links and an opposite end portion connected to said pair of needle holders for rotating said needle holders toward and away from each other.

5. The suturing device recited in claim 4 wherein each of said means for grasping and releasing said end portions of said needles includes a cam pivotally mounted to an exterior portion of each needle holder, said cam arranged on each of said needle holders for contacting and rotating each other when said needle holders are brought adjacent to each other to simultaneously grasp and release said end portions of said needle.

6. A surgical suturing device comprising: a needle, said needle having a thread end portion and a pointed end portion; a pair of pivotally connected needle holders, each of said needle holders having an end portion for grasping one of said end portions of said needle, each of said needle holder end portions having a movable tapered wedge and a fixed end portion for grasping one of said needle's end portions, each of said needle holders further having a latch for simultaneously grasping one end portion of said needle and releasing an opposite end portion of said needle; and a pair of handles for simultaneously actuating said means for grasping and releasing said opposite end portions of said needle.

7. A surgical suturing device comprising a needle, said needle having a thread end portion and an opposite pointed end portion; a first elongated needle holder, said needle holder having an end portion for grasping and releasing said thread end portion of said needle; a second elongated needle holder pivotally connected to said first needle holder and having an end portion for grasping and releasing said opposite pointed end portion of said needle; a bracket having an angular slot attached to an end portion of each of said needle holders; a thin elongated rod having an end portion connected to said angular slot of each of said needle holders and an opposite end portion connected to a movable handle; a fixed handle; a movable handle pivotally connected to said fixed handle.

8. In a surgical suturing device for closing a wound or an incision, the improvement comprising: a needle having a thread end portion and a pointed end portion; a fixed handle; a movable handle pivotally connected to said movable handle; a thin elongated rod having an end portion connected to said movable handle and an opposite end portion connected to a pair of needle holders; a pair of needle holders, each of said needle holders having a means actuated by rotating said needle holders to a closed position adjacent to each other for alternately and simultaneously grasping one of said end portions of said needle and releasing the opposite end portion of said needle.

9. A surgical suturing device comprising: a needle having a thread end portion and an opposite pointed end portion; a first elongated needle holder, said needle holder having an end portion for grasping and releasing said thread end portion of said needle; a second elongated needle holder pivotally connected to said first needle holder, having an end portion for grasping and releasing said opposite pointed end portion of said needle; said needle holders being selectively rotatable between a closed position wherein side portions of said needle holders are adjacent to each other and an open position wherein said side portions are angularly apart from each other; and a means for simultaneously rotating said needle holders to said position adjacent to each other, releasing said thread end portion of said needle in one of said needle holders and grasping said pointed end portion of said needle in said other needle holder.

* * * * *